United States Patent [19]

Sugano et al.

[11] Patent Number: 4,461,760

[45] Date of Patent: Jul. 24, 1984

[54] ANTICANCER DRUGS

[75] Inventors: Nobuhiko Sugano, Toyama; Chiyokichi Iizuka, Noda; Hiroaki Maeda, Chiba, all of Japan

[73] Assignee: Noda Shokukin Kogyo Co., Ltd., Chiba, Japan

[21] Appl. No.: 396,294

[22] Filed: Jul. 8, 1982

[30] Foreign Application Priority Data

Dec. 29, 1981 [JP] Japan .................................. 56-214299

[51] Int. Cl.³ ...................... A61K 37/02; C12P 21/00; C12P 1/02; C12P 19/02
[52] U.S. Cl. ...................................... 424/177; 435/68; 435/72; 435/171
[58] Field of Search ................... 424/177; 435/68, 72, 435/171

[56] References Cited

U.S. PATENT DOCUMENTS 4,289,688  9/1981  Hotta et al. ..................... 424/177
4,357,323  11/1982  Soma et al. ..................... 424/177

OTHER PUBLICATIONS

Park et al., *Seoul University Journal of Pharmaceutical Sciences*, vol. 4, 1979, p. 19.
Tanaka, *National Cancer Center Research Institute*, GANN, 58, 1-4; Feb. 1967, pp. 1-4.
Matsuo et al., *Arzneinittel Forschung*-Drug Research, 32(1), 1982, pp. 647-656.

*Primary Examiner*—Delbert R. Phillips
*Assistant Examiner*—F. T. Moezie
*Attorney, Agent, or Firm*—Abelman, Frayne, Rezac & Schwab

[57] ABSTRACT

Anticancer drugs consisting of sugar and protein composed primarily of xylose which are obtained from the nutrient medium and tissue-medium of Basidiomycetes such as *Lentinus edodes* which has been cultured in a solid medium rich is xylose such as bagasse is described.

5 Claims, 5 Drawing Figures

ANTICANCER DRUGS

BACKGROUND OF THE INVENTION

The present invention relates to anticancer drugs consisting of sugar and protein which is composed primarily of a xylose component contained in the nutrient medium and tissue-medium of Basideomycetes such as *Lentinus edodes* which has been cultured in a solid medium which is rich in xylose, such as bagasse.

The present inventors have researched the mycelia of edible mushrooms belonging to Basidiomycetes such as *Lentinus edodes,* and accomplished many inventions as to the method of extracting pharmacologically active components contained in the mycelia, while the present inventors found out that an active substance of the cytokinin system is contained in the extract of the mycelia and that its extract is effective on vegetable viruses (Japanese Published Specification No. 55-34769).

It has been also known that the fruiting bodies and mycelia of Basidiomycetes and bagasse contain individually an anticancer substance and that the substance is a glucan or peptide glucan which is a structural component of a cell wall.

The main action mechanism of the anticancer substance extracted from the above-described substances is usually an increase of immunity, that is, it serves as an adjuvant; synthetic anticancer drugs developed hitheretofore attack not only cancerous cells but normal ones and cause severe side effects.

BRIEF SUMMARY OF THE INVENTION

The main purpose of the present invention is to propose anticancer drugs which have an excellent anticancer effect.

Another purpose of the present invention is to propose anticancer drugs which have excellent effects for preventing cancer and for promoting the survival of patients having cancer.

Another purpose of the present invention is to propose anticancer drugs which attack only cancerous cells and not normal cells and therefore are very safe.

DETAILED DESCRIPTION OF THE INVENTION

Figure 1:
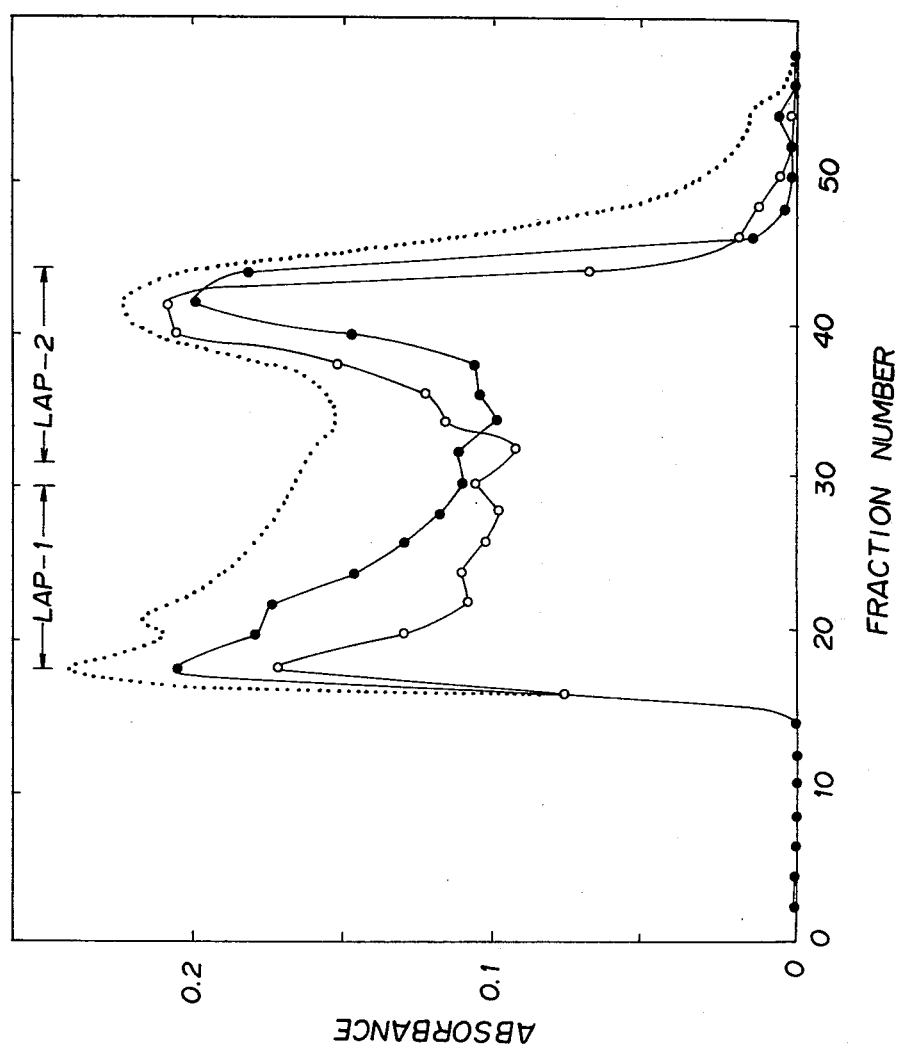
FIG. 1 illustrates the development of fractions obtained with a substance of the present invention by Column Sephalose 6B.

The present inventors have been engaged for many years in research on the method of extracting an anticancer substance from the nutrient medium and tissue-medium of Basidiomycetes such as *Lentinus edodes,* and found some method for the purpose but the active component of this extract is still unknown.

The present inventors have invented a method in which *Lentinus edodes* or other mycelia belonging to Basidiomycetes is cultivated in a solid medium consisting of main fibrous component such as bagasse with rice bran added thereto, and anticancer substance is extracted from the nutrient medium and tissue-medium; Japanese Patent Application No. 90265/1981 (6/12/1981) was filed. In the invention, the active component is not revealed. The present invention is characterized by analyzing the extracted substance in the above-described invention and defining it.

The present inventors analyzed the extracted solution obtained by the method in the above-described invention and found that the solution was rich in sugar and protein primarily composed of a xylose component: moreover, as the result of analyzing the medium, it was found that bagasse (strained lees of sugar cane) and rice bran contain much xylose. Then, the present inventors recognized that sugar and protein primarily composed of xylose contribute the anticancer mechanism.

In the present invention, a medium being rich in xylose must be employed by the reason described above. There are available bagasse, rice straw, straw, stems and leaves of corn and unifoliate plants such Japanese cedar as the material, and rice bran as the nutritional source for such medium. Particularly, bagass has been almost useless hitheretofore and mostly burnt, and consequently it can be obtained easily and cheaply.

As Basidiomycetes used in the present invention, there are *Lentinus edodes, Pleurotus ostreatus, Flammulina Velutipes sing, Ploliata nameko, Lyophyllum aggregatum,* etc., and the substance extracted from the nutrient medium and tissue-medium of *Lentinus edodes* is shown to have the highest anticancer activity.

The substance obtained by the method of the present invention was fractioned by column chromatography with Sephalose 6B and analysed by gas chromatography; it was found to contain sugar and protein primarily consisting of xylose.

The substance obtained by the method of the present invention is excellent particularly in the "anticancer" effect, and it results in an excellent effect on depressing the carcinogenic activity of carcinogens, that is prevention of cancer and prolongation of survival of subjects bearing an autocarcinogenic condition, and also it is found that the substance acts only upon cancerous cells without any detrimental side effect.

The present invention is described by example.

Example

A solid medium consisting of 90% of crushed bagasse, 5% of rice bran and 5% of nutritional material such as wheat bran was sterilized as usual, and the solid seed mycelium of *Lentinus edodes* was inoculated on it. The inoculated medium was then put in a culture room kept at a temperature of 18° to 20° C. at a humidity of 60% by airconditioning and the culture of the mycelium was begun.

When finishing the culture, the medium was transferred into a culture room and allowed to stand there. When fruiting bodies began to grow up from the surface of the medium, the medium was taken out of the culture room, and crushed into thumb sized pieces by a crusher.

The crushed medium (the mixture of mycelium and the medium, which is called the nutrient medium and tissue-medium hereinafter) was packed in a tank, and after adding 5 liters of water at pH 3 to 8 per 800 grams of the nutrient medium and tissue-medium, it was blended and stirred stepwise for a given period of time: that is the temperature was changed in the range from 40° C. to 60° C. depending on pH for promoting enzymation according to activities of enzymes such as cellulase, chitinase, glocosidase and protease existing in the nutrient medium and tissue-medium. Finally it was blended and stirred at 80° C. for deactivating the enzymes, and in this step the mycelial components, the metabolites of mycelia, and cellulose decomposition products of the medium component were dissolved in water.

The suspension thus obtained was packed in a filtering bag of flannel, and compressed to filter, and the filtrate was further filtered through a membrane filter and sterilized to obtain an extracted solution.

The extracted solution thus obtained was freeze-dried and a powder (which is called as LEM hereinafter) was obtained. To the aqueous solution of LEM, ethyl alcohol of 4-fold volume of the LEM solution was added, and the precipitate produced was washed with 80% ethyl alcohol twice, and then centrifuged and freeze-dried to obtain a powder (which is called as LAP hereinafter).

LAP occurred as brown powder; the melting point was vague. It was carbonized on ignition, was insoluble in usual organic solvents, and highly soluble in water.

(1) Preparation of LAP-1 and LAP-2

LAP obtained as described above was dissolved in a small amount of water, fractionated by column chromatography with Sephalose 6B and subjected to the determination of sugar and protein according to Lowry's method and to the anthrone-$H_2SO_4$ method. The result is shown in FIG. 1.

The figure shows the absorbance at 280 nm by dotted line, at 66 nm by Lowry's method by ———O———, and at 620 nm by the anthrone-$H_2SO_4$ method by ———O———. LAP was roughly divided into two fractions; LAP-1 contained the fractions from No. 14 to No. 30 and LAP-2 contained those from No. 31 to No. 42: they were both freeze-dried. The total yield of LAP was more than 95%, and the weight ratio of LAP-1/LAP-2 was about ½.

Both fractions were mainly composed of sugar and protein as seen in Table 1; LAP-1 occurred as a brown, glossy and pasty powder and LAP-2 did as a pale brown, glossy and fine powder.

TABLE 1

| Fraction | μg/mg fraction | | |
|---|---|---|---|
|  | Protein | Sugar | Others |
| LAP | 248 | 576 | 176 |
| LAP-1 | 340 | 652 | 8 |
| LAP-2 | 168 | 484 | 348 |

(2) Amino Acid Composition

Table 2 shows the amino acid composition in LAP, LAP-1 and LAP-2 fractions. All of these fractions were mainly composed of aspargic acid, glutamic acid, glycine, and serine; cysteine was present in large quantity in LAP-2, about 5 times the amount as in LAP-1.

TABLE 2

| Amino acid | Molar % | | |
|---|---|---|---|
|  | LAP | LAP-1 | LAP-2 |
| Aspargic acid | 19.1 | 17.0 | 16.7 |
| Threonic acid | 5.4 | 7.6 | 6.2 |
| Serine | 10.1 | 10.3 | 9.7 |
| Glutamic acid | 14.8 | 14.5 | 14.4 |
| Proline | 0 | 0 | 0 |
| Glycine | 13.3 | 14.8 | 15.4 |

TABLE 2-continued

| Amino acid | Molar % | | |
|---|---|---|---|
|  | LAP | LAP-1 | LAP-2 |
| Alanine | 7.9 | 9.3 | 7.6 |
| Cysteine | 4.6 | 1.8 | 8.7 |
| Valine | 4.0 | 5.0 | 3.8 |
| Methionine | 0.7 | 0.8 | 1.3 |
| Isoleucine | 2.2 | 3.3 | 2.1 |
| Leucine | 2.6 | 3.9 | 2.2 |
| Tyrosine | 0.5 | 0.7 | 0.4 |
| Phenylalanine | 1.7 | 2.3 | 1.2 |
| Histidine | 2.2 | 1.9 | 2.1 |
| Lysine | 6.0 | 4.2 | 5.2 |
| Arginine | 4.9 | 2.5 | 2.9 |

(3) Sugar Composition

Table 3 shows the sugar composition of LAP, LAP-1 and LAP-2. Each of them contained much xylose, and also contained considerable amounts of glucose, galactose, mannose, and arabinose. It is seen that the fruit body of Lentinus edodes is mainly composed of glucose and mannose, and its mycelium mainly consists of glucose. From bagasse and rice bran in the medium, considerable amounts of galactose, arabinose, and xylose were detected, as well as glucose.

TABLE 3

| Sugar | Weight % | | | | | | |
|---|---|---|---|---|---|---|---|
|  | LAP | LAP-1 | LAP-2 | Mycelium | Fruit body | Bagasse | Rice bran |
| Glucose | 19.9 | 13.5 | 20.3 | 80.2 | 40.0 | 63.5 | 53.8 |
| Galactose | 20.3 | 15.3 | 23.2 | 6.5 | 6.7 | 18.0 | 9.6 |
| Mannose | 9.5 | 8.7 | 8.0 | 10.9 | 37.7 | 3.4 | 1.2 |
| Xylose | 30.2 | 39.0 | 30.4 | 0.6 | 0.2 | 4.1 | 10.8 |
| Arabinose | 17.4 | 20.7 | 14.3 | 1.2 | 15.0 | 11.0 | 24.6 |
| Fucose | 1.6 | 1.5 | 2.9 | 0.4 | 0.2 | 0.0 | 0.0 |
| Rhamnose | 1.1 | 1.3 | 0.9 | 0.2 | 0.2 | 0.0 | 0.0 |

As shown in Table 1, the sugar content was about 60% in LAP and LAP-1 and about 50% of LAP-2.

According to the above-described results, the carcinostatic agent of this invention is found to be sugar and protein mainly consisting of xylose.

(4-1) Experiments and Methods (I)

(A) Azo-pigment Liver Cancer

Wister male rats (5-weeks of age) were fed with 0.06% 3'-methyl-4-dimenthylaminoazobenzene (mDAB) assorted food (Nippon Clean Co.) for 6 months and then with usual food to induce liver tumor.

(B) Ascitic Liver Cancer Cells

The ascitic cell obtained from tumor-bearing rats with AH414 of liver cancer derived from 4-dimenthylaminoazobenzene (from Dr. Sasaki, Sasaki Laboratories) was subinoculated into Donryu male rats (140~150 grams) and used in the experiment.

(C) LEM Administration

LEM powder was solved in 0.9% salt water, and given with a dose of 700 mg/kg every other day for 10 days from the beginning of feeding and every two days for further 30 days with a dose of 250 mg/kg every 2 days for further 60 days and with a dose of 100 mg/kg for every 4 days since then; for the survival test, it was given every 2 days with a dose of 300 mg/kg. It was all injected intraperitoneally. In the proliferation test of ascitic cells, 50 mg or 100 mg of LEM per rat was injected intraperitoneally just before inoculation and then every other day 4 times at all. After 8 days, they were subject to laparotomy and the cell count and the quantity of ascites was determined.

(D) LEM Administration and Body Weight Change

Figure 2:
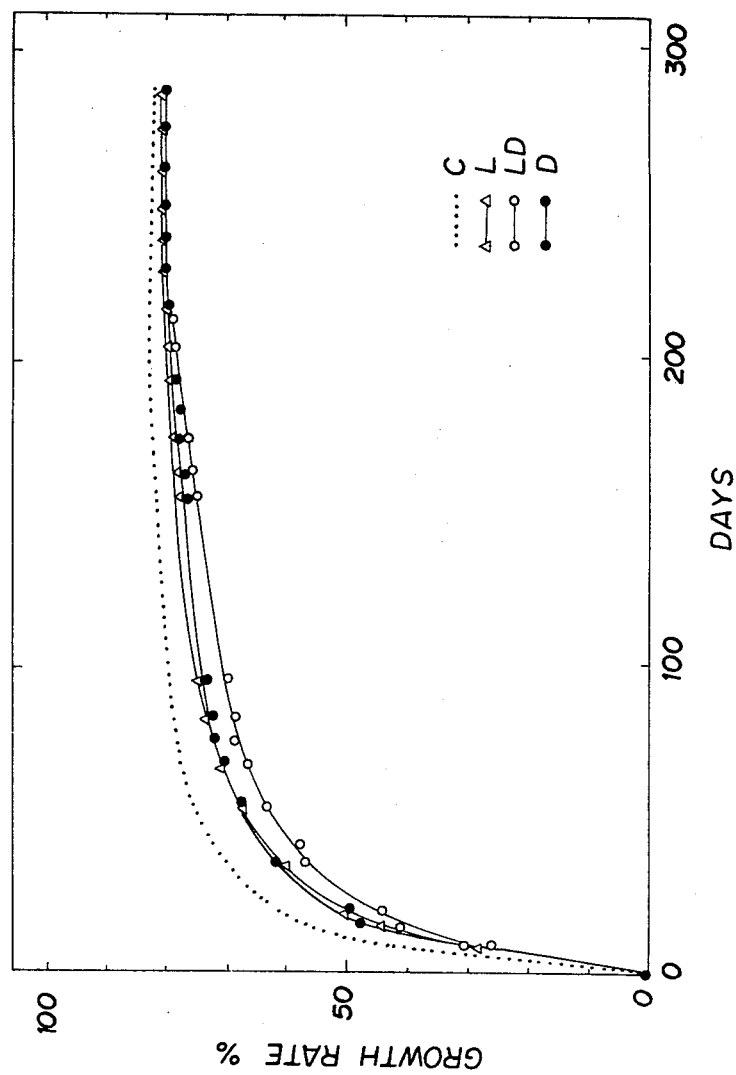
FIG. 2 is a graph showing the body weight gain in rats after giving LEM or DAB.

FIG. 2 shows the body weight gain ((Weight on determination-Weight at the beginning of feeding)/Weight on determination)×100 of rats given LEM or mDAB. C is a group fed with usual food and given 0.9% salt water, L is a group fed with usual food and given LEM; LD is a group fed with mDAB assorted food and given LEM and D is a group fed with mDAB assorted food and given 0.9% salt water. The weight gains of the groups except Group C were lower than that of Group C by 5 to 15% in the feeding period of 100 to 150 days.

(E) LEM Administration and Liver Weight Change

The ratio of the liver weight to the body weight (%) in 41 weeks of feeding (287 days) was about 16% in Group D, 9% in Group LD, 4% in Group L and 3.5% in Group C (Table 4). The rate to depress the liver weight gain in Group LD to Group D ((the liver weight of Group D)−(the liver weight of Group LD)×1/the liver weight of Group D) was 14.0% in 23 weeks of feeding and 50.6% in 41 weeks (Table 5). The liver of Group L had a hue similar to that of Group C, but the liver of Group LD was dark brown in the period of 700 mg/kg administration, suggesting LEM accumulation in the liver.

TABLE 4

The ratio of liver weight gain to body weight by production of azopigment liver cancer and LEM administration

| Weeks | Ratio, % | | | |
|---|---|---|---|---|
| | C | L | LD | D |
| 3 | 3.67 ± 0.35 (3) | 4.49 ± 0.60 (5) | 4.81 ± 0.66 (7) | 3.96 ± 0.46 (7) |
| 8 | 3.64 ± 0.25 (3) | 4.03 ± 0.26 (5) | 4.92 ± 0.63 (7) | 3.80 ± 0.41 (7) |
| 14 | — | 3.49 ± 0.40 (3) | 4.66 ± 0.49 (5) | 4.21 ± 0.83 (5) |
| 18 | 3.65 ± 0.43 (3) | 3.57 ± 0.31 (3) | 4.65 ± 0.56 (3) | 4.41 ± 0.69 (3) |
| 23 | — | 3.34 ± 0.39 (3) | 5.05 ± 0.68 (3) | 4.93 ± 0.63 (3) |
| 41 | 3.50 ± 0.31 (3) | 3.98 ± 0.32 (8) | 8.92 ± 3.97 (8) | 16.14 ± 6.70 (8) |

The figures in the parentheses is the number of rats

TABLE 5

Liver weight gain by production of azopigment liver cancer and LEM administration

| Weeks | Liver weight, g | | | | Sr % |
|---|---|---|---|---|---|
| | C | L | LD | D | |
| 3 | 9.77 ± 1.10 (3) | 10.20 ± 0.99 (5) | 9.06 ± 1.93 (7) | 9.24 ± 1.30 (7) | — |
| 8 | 15.37 ± 1.36 (3) | 12.70 ± 1.35 (5) | 13.19 ± 1.96 (7) | 12.23 ± 2.05 (7) | — |
| 14 | — | 14.20 ± 0.69 (3) | 15.68 ± 2.19 (5) | 15.92 ± 3.14 (5) | — |
| 18 | 16.63 ± 1.07 (3) | 15.77 ± 0.70 (3) | 18.10 ± 4.29 (3) | 17.93 ± 1.46 (3) | — |
| 23 | — | 16.34 ± 0.42 (3) | 19.83 ± 3.19 (3) | 23.07 ± 1.95 (3) | 14.0 |
| 41 | 21.53 ± 2.25 (3) | 20.76 ± 3.49 (8) | 43.73 ± 16.80 (8) | 88.59 ± 41.07 (8) | 50.6 |

The figure in the parentheses denotes the number of rats.
Sr: the rate of suppressing liver weight gain in Group LD.

(F) Survival Rate

Figure 3:
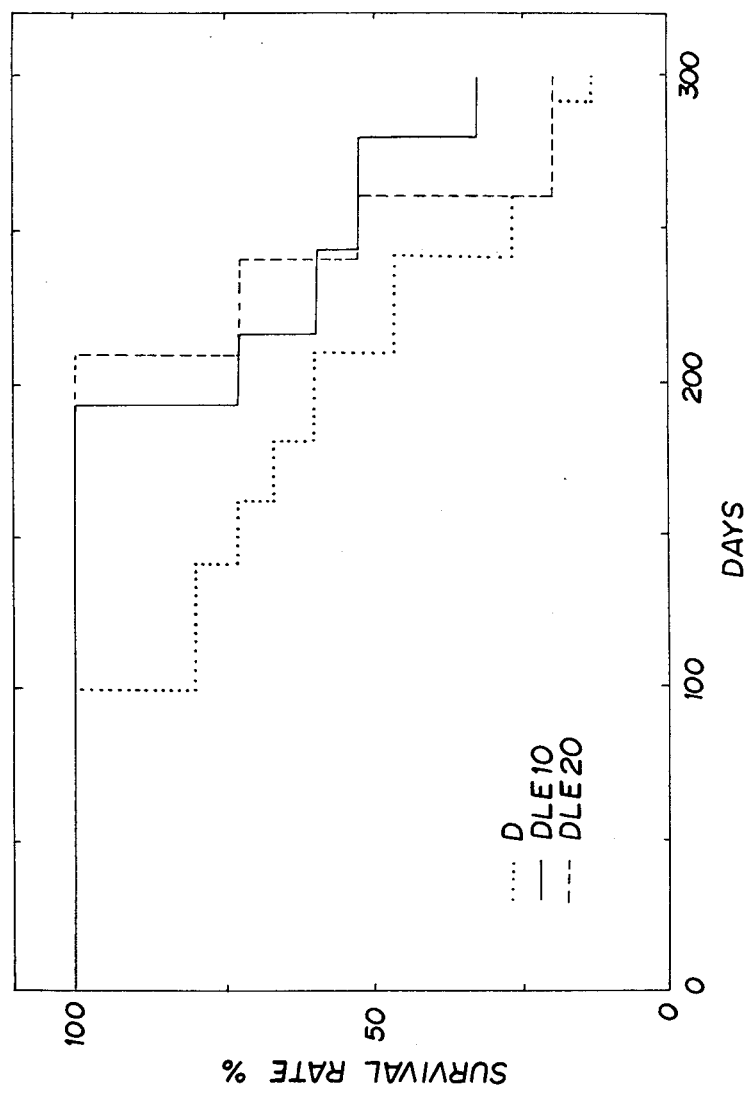
FIG. 3 is a graph showing the survival effect of LEM or DAB treatment.

Rats were fed with mDAB assorted food for 10 weeks or 20 weeks and then LEM was given. The 50% survival rate was 209 days in the non-treated group (D), 260 days in the group given LEM after 20 weeks of feeding (DLE20), and 279 days in the group given LEM after 10 weeks of feeding (DLE10) (FIG. 3).

(G) LEM Administration and Ascitic Cells

Table 6 shows the proliferation of ascitic cells after LEM administration. The value is the average of 3 rats having the largest, the mean and the smallest body weights among 10 rats in the experiment which was repeated twice. The number of cells in 1 ml of ascites was small in the LEM given group; the ratio to the non-treated group (AS) was 52% in the group given 50 mg LEM (ASLE50), and 22% in the group given 100 mg LEM (ASLE100). In addition, the value obtained by multiplying the number of cells by the amount of ascites (the total number of cells) was small, and the ratio (%) was 58.3% in the ASLE50 group and 24.6% in the ASLE100 group. When observing the ascites of the group which was given LEM under a phase contrast microscope, the diameter and the shape of cell were various and masses of cells were scattered: particularly in the ASLE100 group the phenomenon was conspicuous and large cellular masses and cells having vacuolar structure were seen.

TABLE 6

Proliferation of the ascitic liver cancer cell AH414 and LEM administration

| Group | cells/ml, × $10^{-8}$ | Sr, % |
|---|---|---|
| AS | 1.68 ± 0.08 | 100 |
| ASLE50 | 0.88 ± 0.21 | 52 |
| ASLE100 | 0.37 ± 0.33 | 22 |

Sr: the value obtained by representing the number of cells in the non-treated group (AS) being 100
ASLE50: a group given 50 mg LEM
ASLE100: a group given 100 mg LEM (H) LAP Administration and Ascitic Cells In 80% ethyle alcohol, about 30% of LEM weight was precipitated. A dose of LEP of the insoluble fraction was decided to be 30% of the above-described dose of LEM (15 or 30 mg), and the experiment was performed is a similar manner. The number of cells per ml of ascites in the LEM group was small, compared with that of the non-treated group (AS), and the ratio was 48% in the 15 mg group (ASLA15) and 39% in the 30 mg group (ASLA30) (Table 7). These results strongly suggest the presence of a material suppressing the proliferation of LEM in the LAP fraction. The fraction is very soluble in water, mainly consists of sugar (about 58%) and protein (about 25%), and the presence of polyphenols is suggested.

TABLE 7

Proliferation of the ascitic liver cancer cell AH414 and lap administration

| Group | cells/ml, × $10^{-8}$ | Sr, % |
|---|---|---|
| AS | 2.12 ± 0.04 | 100 |
| ASLA15 | 1.02 ± 0.11 | 48 |
| ASLA30 | 0.82 ± 0.08 | 39 |

Sr: the value obtained by representing the number of cells in the non-treated group (AS) being 100
ASLA15: a group given 15 mg LAP
ASLA30: a group given 30 mg LAP (I) Results LAP which is a carcinostatic fraction of LEM is very soluble in water but not soluble in alcohol, and more than 80% of it consists of sugar and protein. There still remained various problems, for example, whether the carcinostatic activity of LAP is due to the synergism in a mixture, due to a single component, or due to the host-mediated effect, and what is the carcinostatic spectrum; however, it is excellent in carcinostatic activity and in survival activity.

(4-2) Ascitic Liver Cancer Cells (A) Ascitic liver cancer cells

AH141 cells derived from the liver cancer induced by 4-dimethylaminoazobenzene (from Dr. Sasaki, Sasaki Laboratories) were subinoculated into Donryu male rats (140~150 grams) and used in this experiment.

(B) LAP-1 and LAP-2 Administration 15 mg of LAP-1 or 10 mg of LAP-2 were injected intraperitoneally just before inoculation of AH414 and then every other day for 6 days, i.e., 4 times at all. On the 8th day the rats were subjected to laparotomy to determine the volume of ascites and the count of cells.

Figure 4:
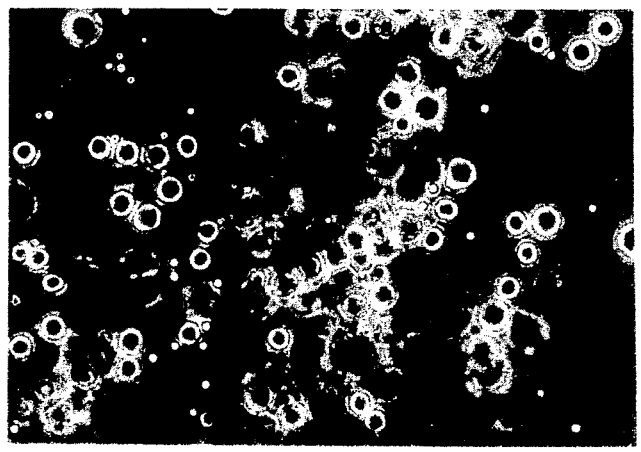
FIG. 4 illustrates a microscopic graph showing the liver cancer cells of a rat given LAP-1 and LAP-2.
Figure 5:
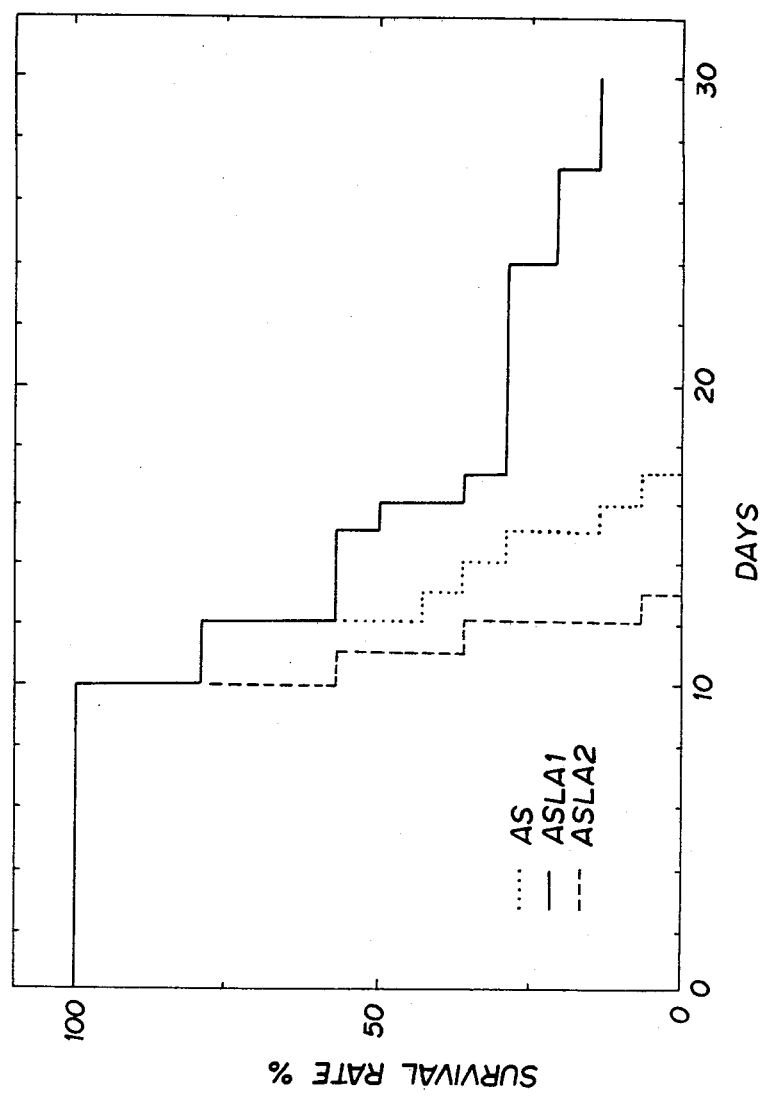
FIG. 5 is a graph showing the survival effect LAP-1 and LAP-2 treatment.

In the LAP-1 and the LAP-2 groups (ASLA1 and ASLA2) the number of cells per ml of ascites was smaller than that in the non-treated group (AS), and the ratio was 68% in the ASLA1 group and 46% in the ASLA2 group (Table 8). However, the value obtained by multiplying the number of cells by the volume of ascites (the total number of cells) was rather large in the ASLA1 group; it is due to the fact that ascites in this group was considerably greater than in the AS group. In addition, the results were obtained from the average values of three rats of the largest, the mean and the smallest body weights among 10 rats in a group in the twice-repeated experiment. In the treated groups some cells were seen to have various cell diameters and outer and inner configurations different from those of the AS group. More than 90% of cells in the AS group were of 10~20 μm in size, while in the ASLA1 group about 40% of all the cells were smaller than 10 μm and 4 to 5% of the rest 60% were larger than 20 μm. In the ASLA2 group about 20% of the cells were smaller than 10 μm and in the remaining 80% of the cells, large cells were found in a ratio similar to that in the ASLA1 group. In the treated groups, many cell-coagulated masses were seen and most of them were strongly stained with Tripan Blue (FIG. 4). In the ASLA1 group some survival effect was seen in 2 or 3 rats in a group comprising 10 rats, and in some rats the ascites disappeared and, in appearance and behavior, were almost similar to those of normal rats (FIG. 5).

TABLE 8

| Group | cells/ml, × $10^{-8}$ | Sr, % |
|---|---|---|
| AS | 1.60 ± 0.61 | 100 |
| ASLA1 | 1.08 ± 0.39 | 68 |
| ASLA2 | 0.73 ± 0.46 | 46 |

(C) Results

The carcinostatic activity in the extract from fruit seed bodies of C.shiitake, Suehirotake, Kawaratake has been precisely and intensively studied, and the active component has now been analyzed. The active component of C.shiitake and Suehirotake is a branched polysaccharide having a main chain of $\beta$-1, 3-glucan, and the active component of Kawaratake is reported to be a protein polysaccharide.

The inventors tried to analyze the active component of the fractions of LAP-1 and LAP-2 in expectation of finding polysaccharide but the result was an unexpected one.

These fractions are mainly composed of xylose, as described above, and also had considerable amounts of glucose, galactose, mannose, and arabinose. These results clearly reflected the polysaccharide composition of the medium, and the fact that xylose is the main sugar in place of glucose strongly suggests the relation with the activity of the enzyme of mycelia of C.shiitake.

It was also revealed that the 2-chain RNA extracted from mycelia and spores of *Lentinus edodes* has an interferon-deriving activity and that a virus-like RNA contained in the fruit seed body of *Lentinus edodes* has a carcinostatic activity.

LAP-1 fraction is eluted at the position of void volume with Sepharose 6B and LAP-2 fraction at the position just prior to total-volume.

Therefore, these fractions are high-molecular weight ones and suggest strongly the presence of xyloglucan and more complicated polysaccharides. It is already known that polysaccharide fractions of bagasse and unifoliate plants such as bamboo have carcinostatic activity, and thus polysaccharide or polysuccharide protein mainly composed of xylose may be expected to have carcinostatic activity. When treating LAP-1 and LAP-2 fractions with 7% polyacrylamide slug gel in electrophoresis and stained with PAS, the LAP-1 fraction shows a strong red-violet band from the base line; when staining with Cumasie Blue, the LAP-2 fraction gives 3 bands at the positions of 75000, 47000, and 32000 molecular weights. Considering the mechanism of the carcinostatic activity of the extract of a fruit seed body of Basidiomycetes reported previously, the carcinostatic activity can be supposed in the LAP-1 fraction as host-mediated activity and in the LAP-2 fraction as another cell-destroying activity. No cytotoxicity is observed in any of LAP, LAP-1 and LAP-2, and no detrimented side effects are observed, such as reduction of white blood cells, atrophy of the spleen and lack of appetite which are noted upon treatment with conventional anticancer drugs.

What we claim is:

1. A composition for treatment of cancer by intraperitoneal or oral administration, consisting of sugar and protein extract, wherein the principal sugar is xylose, obtained from the nutrient- and tissue-medium of *Lentinous edodes,* the method comprising the steps of:

(A) culturing the mycelia of *Lentinus edodes* in a solid medium primarily composed of a xylose-rich bagasse, (B) crushing the mixture of nutrient- and tissue-medium of the mycelia of *Lentinus edodes* and, after adding 5 liters of water per 800 grams of crushed material at a pH of 3 to 8, blending and stirring the nutrient medium and tissue medium at a temperature of from 40° to 60° C., (C) compressing, filtering and sterilizing the suspension obtained from Step B, (D) freeze-drying the filtrate from Step C to form a powder called LEM, (E) dissolving the LEM powder in water and then precipitating a powder, using a four-fold volume of ethyl alcohol, washing the precipitate with an 80% ethyl alcohol solution, and then centrifuging and freeze-drying the resulting material to obtain a powder, called LAP, and (F) fractionating the LAP obtained from Step E by column chromatography on Sephalose to obtain LAP-1 and LAP-2.

2. The anticancer drugs described in claim 1, in which the solid medium of the culture is composed of bagasse and rice bran.

3. The anticancer drugs described in claim 1, in which the Basidiomycetes used is *Lentinus edodes.*

4. An anticancer composition comprising an anticancer effective amount of an anticancer drug as defined in claim 1, in a pharmaceutically effective carrier.

5. A method of treating patients having cancer which comprises administering to said patients an anticancer effective amount of a composition as defined claim 4.

* * * * *